(12) United States Patent
Cetola

(10) Patent No.: US 8,943,700 B2
(45) Date of Patent: Feb. 3, 2015

(54) MODULAR SCALPEL WITH RETRACTABLE BLADE

(75) Inventor: Michael A. Cetola, Wilmington, DE (US)

(73) Assignee: Micro Edge, Inc., Wilmington, DE (US)

( * ) Notice: Subject to any disclaimer, the term of this patent is extended or adjusted under 35 U.S.C. 154(b) by 575 days.

(21) Appl. No.: 12/913,219

(22) Filed: Oct. 27, 2010

(65) Prior Publication Data
US 2011/0106122 A1 May 5, 2011

Related U.S. Application Data (60) Provisional application No. 61/280,399, filed on Nov. 4, 2009.

(51) Int. Cl.
| | | |
|---|---|---|
| B25G 1/00 | (2006.01) | |
| B25G 1/04 | (2006.01) | |
| A61B 17/3213 | (2006.01) | |
| A61B 17/3215 | (2006.01) | |
| A61B 17/00 | (2006.01) | |
| A61F 9/013 | (2006.01) | |

(52) U.S. Cl.
CPC ......... *A61B 17/3213* (2013.01); *A61B 17/3215* (2013.01); *A61B 2017/0046* (2013.01); *A61F 9/0133* (2013.01)
USPC ................................. 30/340; 30/342; 30/162

(58) Field of Classification Search
USPC ........... 30/162, 151, 286, 335, 293, 344, 340; 606/166–172, 181; 81/177.85
See application file for complete search history.

(56) References Cited

U.S. PATENT DOCUMENTS

| | | | | |
|---|---|---|---|---|
| 3,176,395 | A | * | 4/1965 | Warner et al. .................... 30/154 |
| 3,657,812 | A | * | 4/1972 | Lee ................................. 30/162 |
| 3,885,308 | A | * | 5/1975 | Gordin ............................ 30/162 |
| 4,170,993 | A | | 10/1979 | Alvarez |
| D263,020 | S | * | 2/1982 | Rau, III ............................ D8/99 |
| 4,337,576 | A | * | 7/1982 | Drost et al. ...................... 30/162 |
| 4,499,898 | A | * | 2/1985 | Knepshield et al. .......... 606/166 |
| 4,516,575 | A | * | 5/1985 | Gerhard et al. ............... 606/170 |
| 4,730,613 | A | * | 3/1988 | Gordy ............................ 606/172 |
| 4,917,679 | A | | 4/1990 | Kronner |
| 5,279,581 | A | | 1/1994 | Firth et al. |
| 5,318,547 | A | | 6/1994 | Altschuler |
| 5,323,765 | A | * | 6/1994 | Brown .......................... 600/104 |
| 5,342,379 | A | * | 8/1994 | Volinsky ....................... 606/167 |
| 5,391,177 | A | * | 2/1995 | Schwartz ...................... 606/167 |
| 5,431,671 | A | | 7/1995 | Nallakrishnan |
| 5,472,430 | A | | 12/1995 | Vaillancourt et al. |
| 5,501,672 | A | | 3/1996 | Firth et al. |

(Continued)

*Primary Examiner* — Omar Flores Sanchez
(74) *Attorney, Agent, or Firm* — Fox Rothschild LLP (57) ABSTRACT

A scalpel (10) having a handle assembly (16) and one of a plurality of modular blade assemblies (18). Each blade assembly includes a casing (46) within which is a retractable rod (48) having a distal end to which is permanently affixed a blade (12), and also includes a spring (56) having an unstressed state wherein the retractable rod and its blade are retracted within the casing. The handle assembly (16) includes a handle casing (20) within which is slidably disposed a handle rod (32) that is manipulatable between a retracted position and an active position with respect to the handle casing. In the active position, the handle rod's distal end engages and pushes the proximal end (66) of the retractable rod (48) to urge the blade (12) distally for performance of a procedure, while in the retracted position, the handle rod (32) permits the retractable rod (48) to self-retract within its casing (46).

10 Claims, 5 Drawing Sheets

(56) References Cited

U.S. PATENT DOCUMENTS

| | | | |
|---|---|---|---|
| 5,591,138 A | 1/1997 | Vaillancourt | |
| 5,665,099 A | 9/1997 | Pilo et al. | |
| 5,688,249 A | 11/1997 | Chang et al. | |
| 5,713,915 A | 2/1998 | Van Heugten et al. | |
| 5,908,433 A * | 6/1999 | Eager et al. | 606/170 |
| 5,984,899 A | 11/1999 | D'Alessio et al. | |
| 6,077,283 A | 6/2000 | Meyer et al. | |
| 6,149,661 A | 11/2000 | Graczyk | |
| 6,261,259 B1 | 7/2001 | Bell | |
| 6,500,187 B1 | 12/2002 | Petersen | |
| 6,544,277 B1 * | 4/2003 | O'Heeron et al. | 606/185 |
| 6,730,062 B2 | 5/2004 | Hoffman et al. | |
| 6,758,836 B2 | 7/2004 | Zawacki | |
| 6,884,240 B1 | 4/2005 | Dykes | |
| 7,296,316 B1 * | 11/2007 | Wu | 7/158 |
| 7,465,294 B1 | 12/2008 | Vladimirsky | |
| 7,556,617 B2 | 7/2009 | Voorhees, Jr. et al. | |
| 2005/0119680 A1 * | 6/2005 | Dykes | 606/167 |
| 2005/0159767 A1 * | 7/2005 | Adams et al. | 606/180 |
| 2007/0191772 A1 | 8/2007 | Wojcik | |
| 2009/0005741 A1 | 1/2009 | Martin et al. | |

\* cited by examiner

MODULAR SCALPEL WITH RETRACTABLE BLADE

CROSS-REFERENCE TO RELATED APPLICATIONS

This application claims priority from U.S. Provisional Patent Application Ser. No. 61/280,399 filed Nov. 4, 2009.

FIELD OF THE INVENTION

This relates to the field of medical devices and more particularly to scalpels.

BACKGROUND OF THE INVENTION

In ophthalmic surgery, and in neurosurgery, intricate incisions must often be made on tissue surfaces that are not planar, e.g., on spherical surfaces such as the eye. This requires the use of fine, precision blades such as diamond blades that have cutting edges of different designs to attain subtly different incisions. Cutting edges and their resultant incisions are disclosed, for example, in U.S. Pat. No. 5,713,915. Scalpel instruments to which such diamond blades are affixed are also known.

Certain scalpels are known in which the blade tip is retractable into the scalpel's distal end for safety reasons; for precision diamond blades, retraction of the blade importantly serves to protect the extremely fragile blade. See U.S. Pat. Nos. 5,342,379 and 5,431,671, wherein the blade is retractable by a spring, and U.S. Pat. No. 5,665,099, wherein the blade is retractable by a vacuum. U.S. Pat. No. 6,884,240 discloses a slidable guard that is movable distally to a locked position to surround and enclose the blade. In U.S. Pat. No. 6,544,277, a scalpel is disclosed wherein a common handle is adapted to receive one of a plurality of blade assemblies disconnectable therefrom, enabling a surgeon to select a blade assembly having the desired blade design. The patent also discloses a plurality of blade cutting edge designs.

It is desired to provide a scalpel assembly wherein a plurality of blade assemblies are each adapted to be easily and quickly connected to and released from a common handle by the surgeon during a procedure, and wherein the blade tip is retractable into the scalpel assembly's distal end by the surgeon when desired.

BRIEF SUMMARY OF THE INVENTION

Briefly, the present invention is a modular scalpel assembly, wherein a handle assembly is adapted to receive affixable thereonto one of a plurality of blade assemblies that are distinguished from each other by the particular blade design or size, or both, and wherein the blade is retractable into its blade assembly for safety and blade protection purposes. The retraction is achieved by a handle rod that is slidable between a first and a second position within its handle casing, with its first or active position forcing the blade from the blade assembly casing for performance of surgery, and with its second or retracted position permitting the blade to self-retract within the blade assembly's casing.

In the preferred embodiment, the blade assembly comprises a blade assembly casing within which is secured a retractable rod having a distal end whereonto is permanently affixed a blade, and having a proximal end engageable and cooperable with the handle rod of the handle assembly. Preferably, the retractable rod is movably secured within the blade assembly casing by an inner collar of the casing; a first fitting is affixed to the retractable rod near a distal end thereof that abuts the inner collar from distally thereof; a second fitting is affixed to the retractable rod at a proximal end thereof; and a compression spring is disposed about a portion of the retractable rod, held between the second or proximal fitting and the inner collar of the casing.

Also, in the preferred embodiment, the handle assembly comprising the handle casing and the handle rod defines an arrangement for relative axial positioning of the handle rod with respect to the handle casing, the preferred arrangement comprising an axially extending slot defined in the handle casing having distal and proximal ends whereat doglegs extend radially to define first and second detents, for active and retracted states of the scalpel, in cooperation with a radially outward pin of the handle rod that is disposed within the axially extending slot upon assembly.

Such a modular scalpel assembly permits easy assembly of the handle assembly and a selected one of the blade assemblies, such as by using male and female threaded connection sections of the respective casings at the connection interface, that permit the open proximal end of the blade assembly to allow access thereto and engagement by the retractable rod's proximal end and the distal end of the handle rod that will urge the retractable rod distally into an active state wherein the blade is exposed for use in surgery. The modular scalpel assembly is easily sterilizable for reuse, and includes a plurality of blade assemblies each having a blade, preferably a diamond, having a particular design to achieve a particular kind of cut, and is especially useful in ophthalmic surgery, neurosurgery and the like, wherein precision cuts of subtle but distinct shapes are essential.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

In the drawings, like numerals indicate like elements throughout. Certain terminology is used herein for convenience only and is not to be taken as a limitation on the present invention. The terms "distal" and "proximal" refer, respectively, to directions closer to and away from a patient for a procedure. The terminology includes the words specifically mentioned, derivatives thereof and words of similar import. The terms and expressions used herein, and the embodiments illustrated below, are not intended to be exhaustive or to limit the invention to the precise form disclosed. These terms, expressions and embodiments are chosen and described to best explain the principle of the invention and its application and practical use and to enable others skilled in the art to best utilize the invention.

Figure 1:
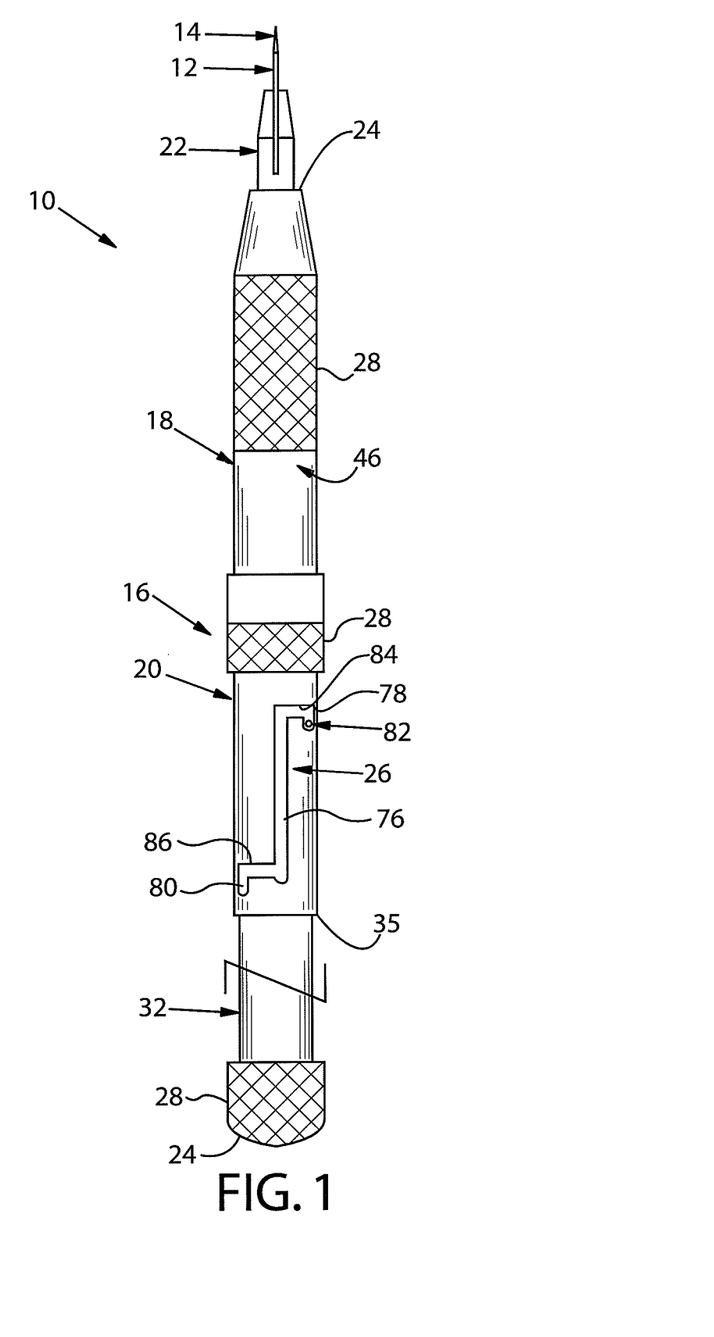
FIG. 1 is a plan view of a scalpel assembly of the present invention, with its blade extended for use.

Scalpel 10 of the present invention is shown in FIG. 1 in an active state with the blade 12 extended distally and having a cutting edge 14, for performance of surgery by the surgeon. The scalpel 10 is an assembly basically of a handle assembly 16 to which is connected a blade assembly 18 at the distal end of the handle assembly. Blade 12 is mounted to a blade mount section 22 protruding distally from blade assembly distal end 24 for use. Handle assembly 16 includes a tubular handle casing 20 within which is disposed a cylindrical handle rod 32, with handle rod 32 being manipulated by its proximal end 24 which has preferably a knurled surface 28 to facilitate gripping by the surgeon. Other knurled surfaces 28 are preferably provided on handle casing 20 and blade assembly casing 46 for the same purpose.

Figure 2:
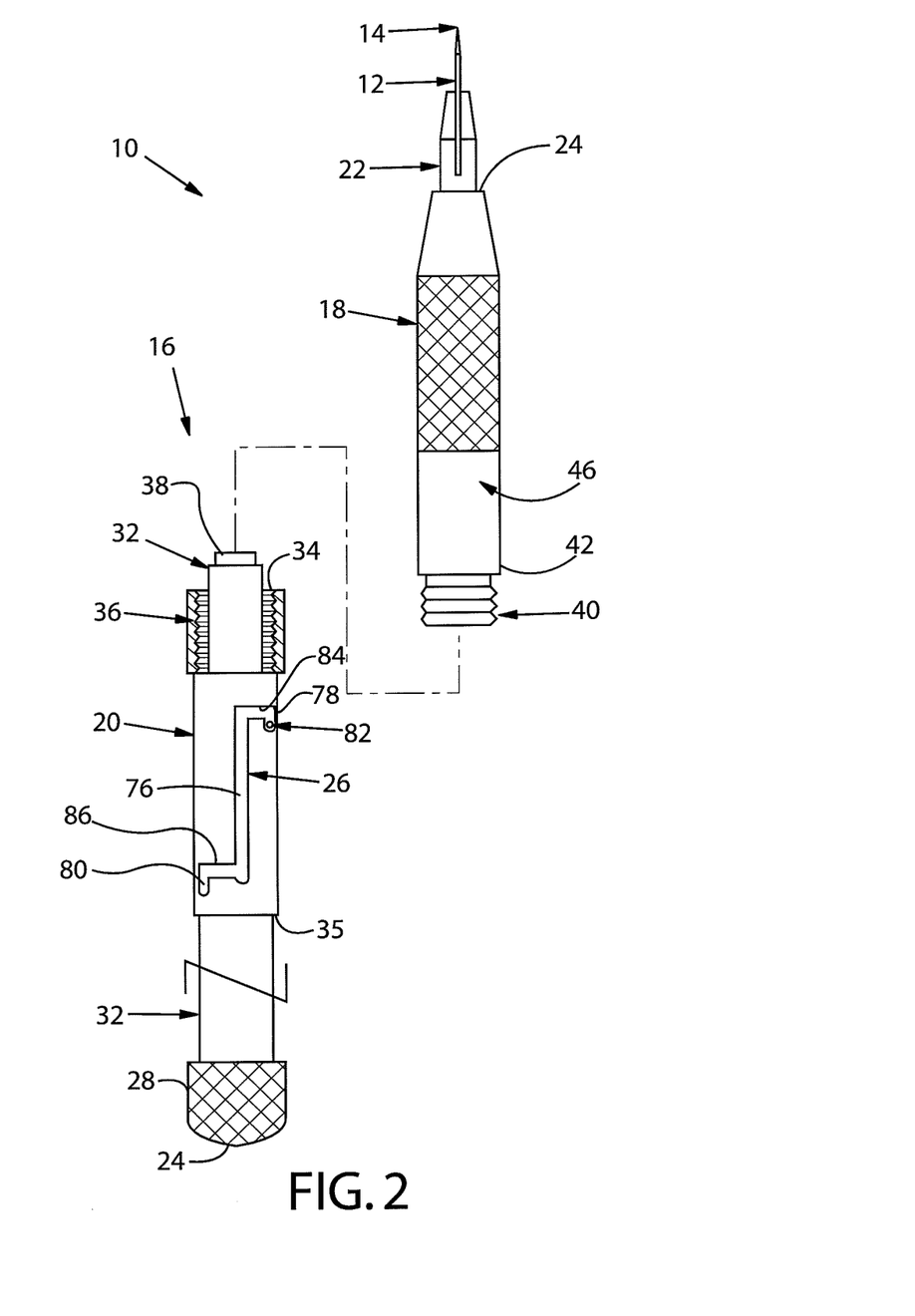
FIG. 2 is a plan view of the scalpel assembly of FIG. 1 with the handle assembly exploded from the blade assembly, in a first or active state wherein the handle rod distal end protrudes from the distal end of the handle casing, and the blade affixed to the retractable rod is shown projecting from the blade assembly casing.
Figure 3:
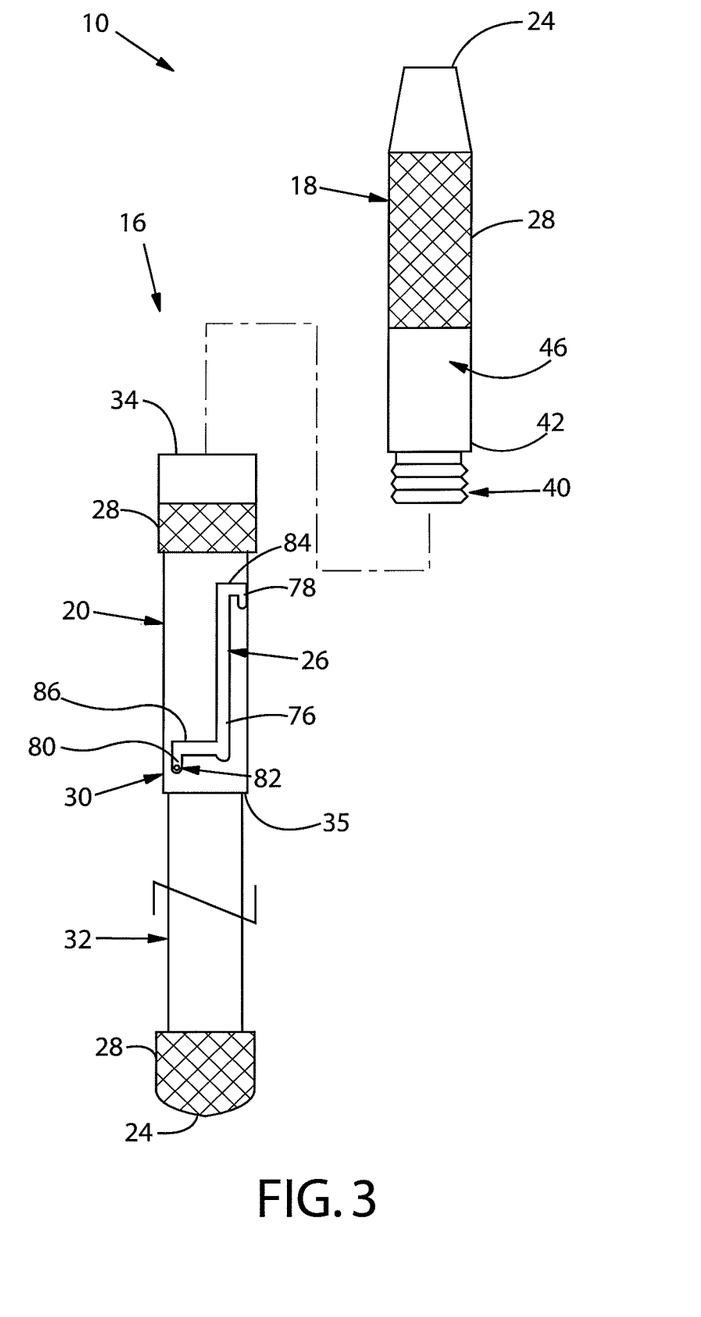
FIG. 3 is a plan view of the scalpel assembly of FIG. 1 with the handle assembly exploded from the blade assembly, in a second or retracted state wherein the handle rod distal end is recessed within the distal end of the handle casing, and the blade affixed to the retractable rod is recessed within the blade assembly casing.

In FIGS. 2 and 3 are shown the handle assembly 16 and the blade assembly 18 separated from each other, with FIG. 2 showing the assemblies as if in the active state in which the blade 12 would protrude from the distal end of the blade assembly 18, while FIG. 3 shows the assemblies as if in the retracted state in which the blade 12 would be recessed within the distal end of the blade assembly 18. It is seen that the blade assembly 18 includes a proximal male threaded section 40 for coupling with and decoupling from a distal female threaded section 36 of the handle assembly 16. Abutment of the proximal end 42 of blade assembly casing 46 with the distal end 34 of the handle casing 20 indicates when the two assemblies are fully coupled. It should be noted that the handle rod 32 includes a distal end portion that projects distally from the handle casing 20 when in the active state, for cooperating with the retractable rod of the blade assembly to urge it distally against spring bias to translate the blade mount section 22 distally for blade 12 to be exposed for surgical use.

Figures 4, 5:
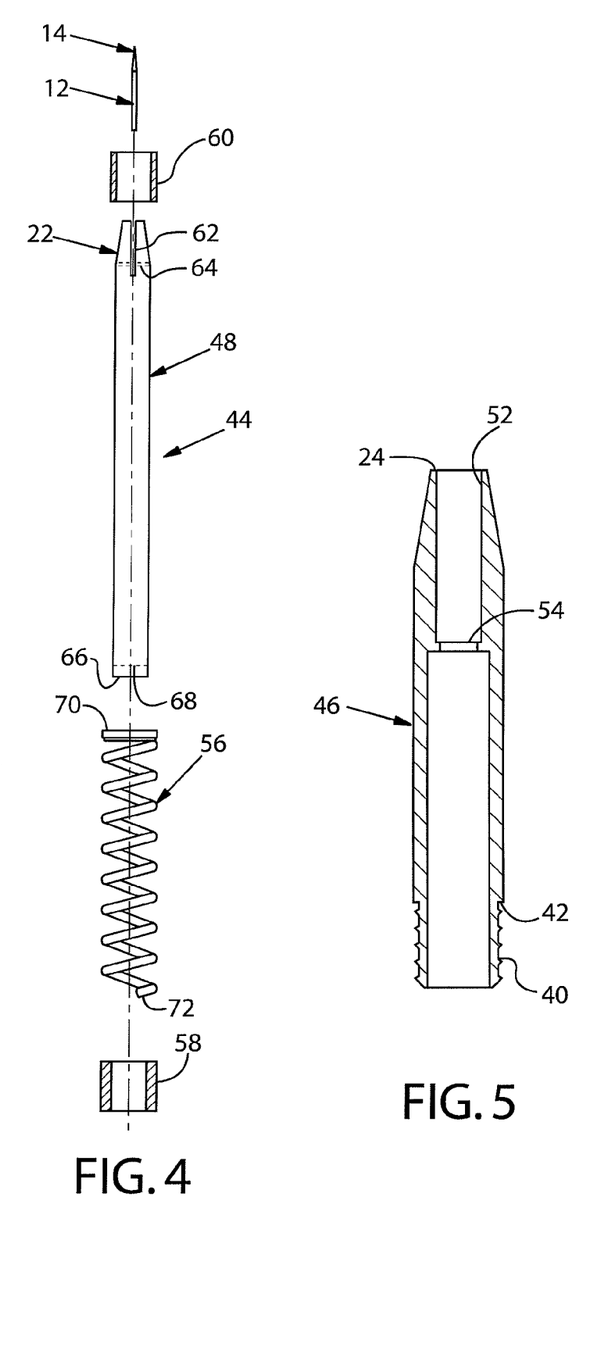
FIG. 4 is an exploded view of the components of the retractable rod and its related components.
FIG. 5 is a cross-sectional view of the blade assembly casing, with its inner collar discernible near its distal end.
Figure 6:
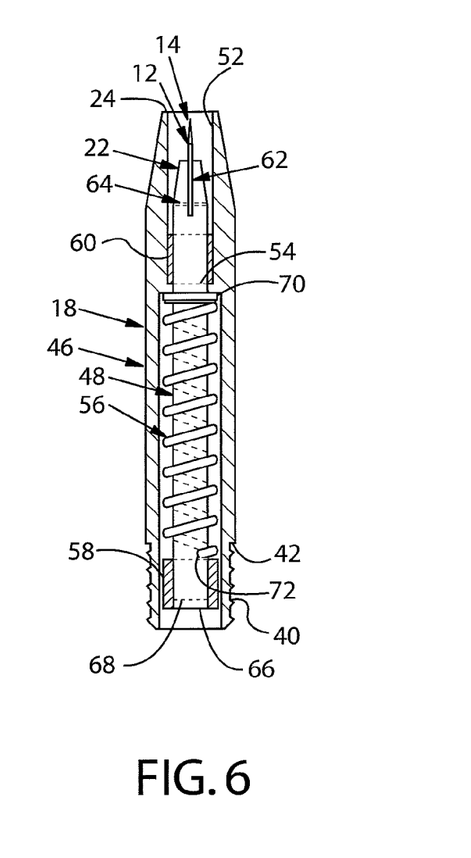
FIG. 6 is a cross-sectional view of the blade assembly as assembled, with the blade shown recessed within the distal end of the blade assembly casing, and the spring disposed between the proximal fitting and the inner collar in a substantially unstressed state.

Referring now to FIGS. 4 to 6, blade assembly 18 is shown in detail, having a cylindrical retractable rod 48 disposed movably within tubular blade assembly casing 46, with a coil spring 56 disposed about the retractable rod 48. Thin diamond blade 12 is affixable into slot 62 into the blade mount section 22 of the retractable rod 48 such as epoxy resin; preferably, small radial holes 64 into the blade mount section 22 permit wicking of the epoxy resin thereinto from the base of slot 62 and form mechanical joints with the retractable rod. A proximal fitting 58 is shown that is force fit, for example, onto the proximal end of retractable rod 48 to define a proximal stop for the proximal end 72 of spring 56. A distal fitting 60 is shown that is force fit, for example, onto the retractable rod 48 just proximally of the blade mount section 22. Blade assembly casing 46 includes defined therewithin an inner collar 54: the inner collar serves as the distal stop for distal end 70 of spring 56 and also as the proximal stop for distal fitting 60. Upon assembly, the retractable rod subassembly is secured within the blade assembly casing by its distal fitting 60 being distal of the inner collar 54, and the trapped spring 56 being proximal of the inner collar 54, all allowing the retractable rod 48 being axially movable within the blade assembly casing 46. Trapped spring 56 is biasable upon engagement of the distal end of handle rod 32 abutting and pressing distally the proximal end 66 of retractable rod 48, which causes the blade mount section 22 and the blade 12 to protrude distally from the distal end of the blade assembly casing 46. Preferably, the handle rod 32 includes a rib 38 receivable into a complementary slot 68 into the proximal end 66 of retractable rod 48 enabling rotation of the retractable rod 48 by handle rod 32, as will be explained hereinbelow.

Referring again to FIGS. 1 to 3, a pin-and-slot arrangement 26 in the handle assembly 16 is shown which is utilized to control retraction and projection of the blade from the scalpel. Handle casing 20 is cylindrical and a slot 76 is defined through the wall of the handle casing generally extending in an axial direction, with a distal dogleg portion 78,84 and a proximal dogleg portion 80,86. A pin 82 projecting radially from the side of handle rod 32 is disposed within the slot 76 and movable therealong between the distal and proximal dogleg portions. Movement of the pin along transverse dogleg portions 84,86 is attained by incremental rotation of the handle rod with respect to the handle casing 20. Seating within the axial portions of the dogleg portions is assured by the handle rod 32 being continuously biased proximally by the force of the spring about the retractable rod within the blade assembly 18.

Assembly and operation of the scalpel is easily performed by the surgeon. A particular blade assembly is selected by the surgeon according to the type of incision needed; the selected blade assembly is threadedly coupled to the handle assembly, during which the distal end of the handle rod 32 (in its "active" state) engages the proximal end 66 of the retractable rod with the rib 38 becoming assuredly seated in the complementary slot 68 by incremental rotation of the blade assembly, all while the spring 56 is being compressed; and, the pin 82 of the handle rod becomes seated within distal dogleg portion 78 by reason of the stored energy of the spring 56 urging the handle rod proximally, whereby the scalpel is locked in the active state.

Retraction of the blade 12 into the blade assembly 18 is achieved simply by urging the handle rod 32 distally against spring bias to align the pin radially with transverse dogleg portion 84 and then rotating the handle rod 32 with respect to the handle casing 20 until the pin 82 is aligned with the main axially extending portion of the slot 76, whereupon the stored energy of the spring 56 urges the handle rod proximally until reaching axial portion 86 of proximal dogleg portion 80, whereupon the blade mount section 22 and blade 12 self-retract into blade assembly casing 46; and, finally, incremental rotation of handle rod 32 enables assured seating of the pin 82 within proximal dogleg portion 80 by reason of stored energy of spring 56, locking the scalpel into the retracted state wherein the blade is withdrawn into the blade assembly casing 46. Preferably, the handle rod 32 remains in engagement with the retractable rod 48 at all times while the handle and blade assemblies are connected, as a result of continuous spring bias. Continuous engagement of the handle and blade assemblies is assured by the continuous spring bias, which in turn assures a smooth transition between active and retracted states. Disassembly of the blade assembly 18 from the handle assembly 16 is easily achieved by retracting the blade into the blade assembly as just described, until the pin becomes seated at the proximal end of the axially extending slot portion 76, whereupon the blade assembly can be unthreaded and disconnected from the handle assembly.

Preferably, the components of at least the handle and retractable rods, and the handle and blade assembly casings are precision machined of a durable, light-weight metal such as titanium. It is preferred that the rods fit snugly within their respective casings to minimize lateral play while also minimizing any friction between the adjacent surfaces during axial movement. It is also preferred that, for the performance of very precise surgery, the blade be a diamond. The assembly is free of lateral projections, and the pin of the handle rod, preferably, does not project beyond the outer surface of the handle casing at the slot.

Figure 7:
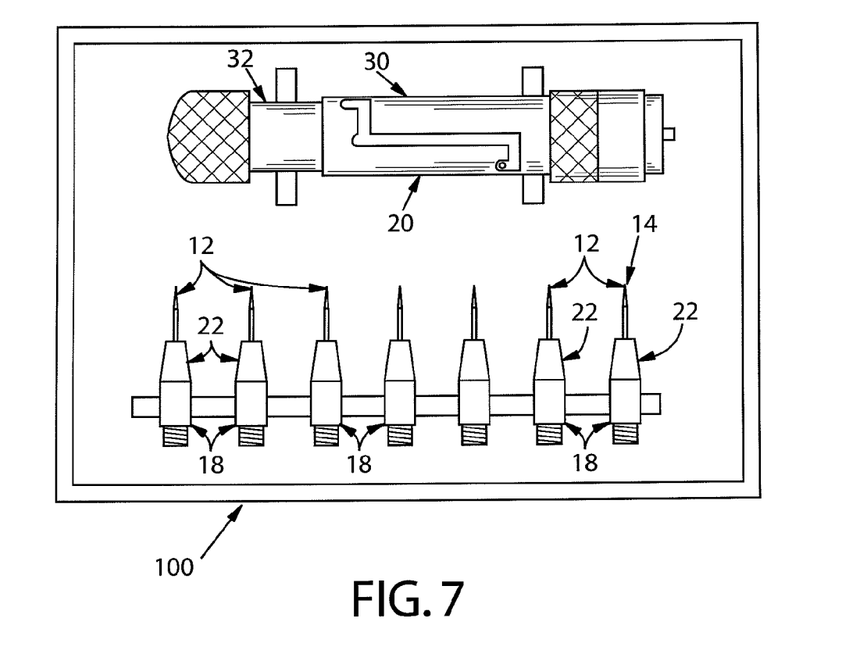
FIG. 7 is a plan view of the scalpel assembly displayed in a tray such as for sterilization, showing the handle assembly and a plurality of representative blade assemblies each having a blade with a different design of cutting edge from the others.
Figure 8:
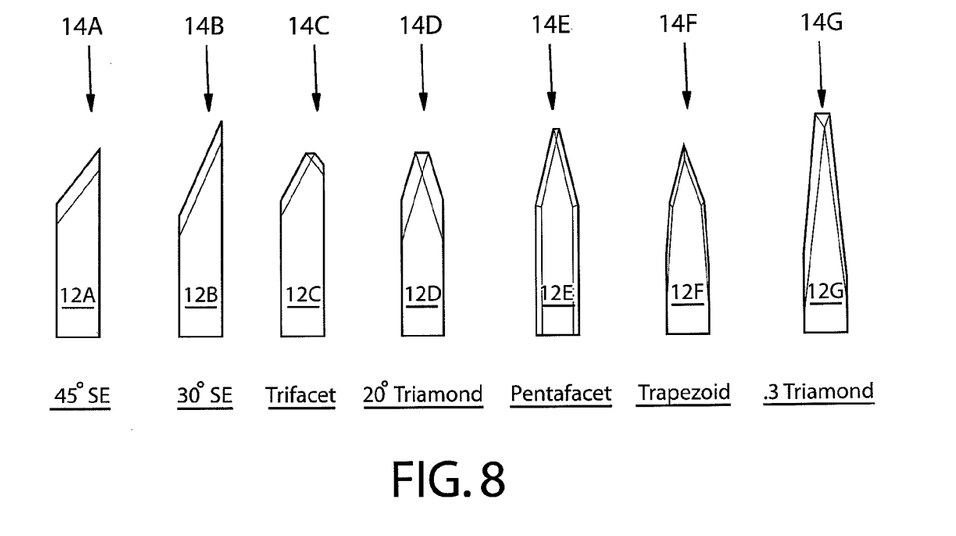
FIG. 8 illustrates a plurality of diamond blades having respectively different designs of cutting edges, or different sizes.

FIG. 7 is representative of a scalpel kit wherein the handle assembly 16 and a plurality of representative blade assemblies 18 are positioned within a tray 100, with the tray preferably permitting sterilization of the kit. An array of blades 12A to 12G with representative distinct designs of blade tips 14A to 14G is shown in FIG. 8, with each blade tip so designed to be utilizable to result in different resultant incisions, as desired by the surgeon; the blade assemblies are held in the active state by portions of the tray (not shown) in order for the blades to be assuredly sterilized. Also, the blades may be of different sizes. At this time, it is estimated that there presently are over fifty different blade designs and sizes in use by surgeons world-wide.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A modular scalpel assembly, comprising:
a handle assembly and at least one blade assembly connectable thereto and separable therefrom, each at least one blade assembly including a blade affixed thereto at a distal end, wherein the scalpel assembly includes a plurality of blade assemblies that are interchangeable with the handle assembly,
wherein the handle assembly with the blade assembly connected thereto is adapted to provide for retraction of the blade into the distal end of the blade assembly and wherein the handle assembly includes a handle casing and a handle rod disposed therewithin and movable therewithin, with the handle assembly having an arrangement that defines a distal-most position for the handle rod and a proximal-most position therefore, wherein a distal end of the handle rod is engageable with a proximal end of a retractable rod within the blade assembly to move the retractable rod to a distal-most position extending the blade thereof for surgical use, when the handle rod is in its distal-most position, and wherein a spring within the blade assembly is under compression when the handle rod is in its distal-most position, wherein the arrangement comprises a slot in the handle casing cooperable with a radially extending pin of the handle rod to permit the pin to travel along the slot, whereby the handle rod moves controllably within the handle casing between the distal-most and proximal-most positions.

2. The scalpel assembly of claim 1, wherein the handle assembly and each at least one blade assembly include respective complementary connection sections adapted for easy connection and disconnection of the handle and blade assemblies.

3. The scalpel assembly of claim 1, wherein at least two of said blade assemblies include respective blades that are different from each other.

4. The scalpel assembly of claim 1, wherein the slot extends axially and includes distal and proximal dogleg portions at least extending transversely with respect to the axial direction.

5. The scalpel assembly of claim 4, wherein the distal and proximal dogleg portions further include at respective ends thereof, proximal dogleg portions defining pin seats.

6. A modular scalpel assembly, comprising:
a handle assembly and at least one blade assembly connectable thereto and separable therefrom, each at least one blade assembly including a blade affixed thereto at a distal end, wherein the scalpel assembly includes a plurality of blade assemblies that are interchangeable with the handle assembly, wherein the handle assembly with the blade assembly connected thereto is adapted to provide for retraction of the blade into the distal end of the blade assembly and wherein the handle assembly includes a handle casing and a handle rod disposed therewithin and movable therewithin, with the handle assembly having an arrangement that defines a distal-most position for the handle rod and a proximal-most position therefore, wherein a distal end of the handle rod is engageable with a proximal end of a retractable rod within the blade assembly to move the retractable rod to a distal-most position extending the blade thereof for surgical use, when the handle rod is in its distal-most position, and wherein the distal end of the handle rod includes a distally extending rib that is received into a complementary slot in the proximal end of the retractable rod at all times when the blade assembly is connected to the handle assembly.

7. A modular scalpel assembly, comprising:
a handle assembly and at least one blade assembly connectable thereto and separable therefrom, each at least one blade assembly including a blade affixed thereto at a distal end, wherein the scalpel assembly includes a plurality of blade assemblies that are interchangeable with the handle assembly, wherein the handle assembly with the blade assembly connected thereto is adapted to provide for retraction of the blade into the distal end of the blade assembly, wherein each blade assembly includes a blade assembly casing and a retractable rod disposed therewithin and movable axially therewithin, with the blade being mounted at a blade mount section at the distal end of the retractable rod, and wherein a spring is disposed about the retractable rod between distal and proximal stops each defined by either by said blade assembly casing or said retractable rod, and wherein the distal stop for said spring comprises an inner collar defined within said blade assembly casing near a distal end thereof, and the proximal stop for said spring is defined by a proximal enlargement at the proximal end of the retractable rod.

8. The scalpel assembly of claim 7, wherein said proximal enlargement is an annular fitting affixed to the retractable rod.

9. The scalpel assembly of claim 7, wherein the inner collar serves as a proximal stop for proximal movement of the retractable rod, the retractable rod having a distal enlargement near its distal end proximal of the blade mount section.

10. The scalpel assembly of claim 9, wherein the distal enlargement is an annular fitting affixed to the retractable rod.

* * * * *